United States Patent [19]

Frigg et al.

[11] Patent Number: 5,041,115
[45] Date of Patent: Aug. 20, 1991

[54] MEDULLARY NAIL FOR THE TIBIA

[75] Inventors: Robert Frigg, Davos; Paul F. Heini, Bern, both of Switzerland

[73] Assignee: Synthes (U.S.A.), Paoli, Pa.

[21] Appl. No.: 530,270

[22] Filed: May 30, 1990

Related U.S. Application Data

[63] Continuation-in-part of Ser. No. 322,937, Mar. 14, 1989.

[30] Foreign Application Priority Data

Mar. 14, 1988 [CH] Switzerland ..................... 00953/88

[51] Int. Cl.[5] .............................................. A61F 5/46
[52] U.S. Cl. ........................................ 606/62; 606/67
[58] Field of Search ..................... 606/53, 60, 62, 64, 606/67

[56] References Cited

U.S. PATENT DOCUMENTS

| | | | |
|---|---|---|---|
| 4,016,874 | 4/1977 | Maffei et al. | 606/62 |
| 4,055,172 | 10/1977 | Ender et al. | 606/62 |
| 4,135,507 | 1/1979 | Harris | 606/62 |
| 4,522,202 | 6/1985 | Otte et al. | 606/62 |
| 4,805,607 | 2/1989 | Engelhardt et al. | 606/27 |

Primary Examiner—Robert A. Hafer
Assistant Examiner—Kerry Owens
Attorney, Agent, or Firm—Davis, Hoxie, Faithfull & Hapgood

[57] ABSTRACT

A hollow one-piece intramedullary nail for the tibia has a proximal end segment, a bent intermediate segment and a distal end segment. The central axis of the proximal end segment diverges from the central axis of the distal end segment at an angle of about 11°; the proximal end segment and the intermediate segment have a total length in the range of about 105 mm; and the sum of the length of the proximal end segment and half of the length of the intermediate segment corresponds to about one third of the total length of the nail.

12 Claims, 1 Drawing Sheet

MEDULLARY NAIL FOR THE TIBIA

This application is a continuation-in-part of pending application Ser. No. 322,937 filed Mar. 14, 1989.

FIELD OF THE INVENTION

The invention relates to a hollow one-piece intramedullary nail for the tibia.

BACKGROUND OF THE INVENTION

The most recent indications for the use of tibia intramedullary nails are simple horizontal or oblique fractures of the tibia, multistage breaks of the tibia shaft, and fragmented breaks of the tibia shaft. Because use of tibia intramedullary nails is now indicated for more fractures of the lower leg, a need to change the shape and nature of the nail has arisen.

Formerly, the basic purpose of an intramedullary nail was to immobilize the bone internally, with the axial force as well as torsional moments being borne by the bone itself. The only function of the nail was to maintain the longitudinal axis of the bone upright. This meant that relatively thin, flexible nails could be used, which have the advantage that they can be adjusted to the medullary cavity. This adjustment is particularly important in the insertion of the nail, since the entry point of the nail is not in line with the longitudinal axis of the bone. The entry point is located on the tuberositas tibia, slightly proximal to the patellar tendon attachment. After the medullary cavity has been opened with an awl and the medullary cavity has been drilled, the nail is driven in. The problem with driving in the nail is that after crossing the medullary cavity, the nail reaches the posterior cortex, and can be driven in further only if its shape is deformed. With soft bones and young patients, the tip of the nail sometimes punctures the posterior cortex.

To prevent a perforation of the posterior cortex, the method known as bunch-nailing (for example, according to German Auslegeschrift AS 23 41 439) has been proposed. In this method, wires approximately 2.0 mm thick are pushed into the medullary cavity. The advantage of this method is that the individual wires are very flexible and can adjust well to the shape of the medullary cavity. In this known method, the medullary cavity is filled up with individual wires, whereupon it becomes possible to splint the bone.

Bunch-nailing has become generally accepted in treating short oblique fractures in the mid-shaft range of the tibia. The disadvantages of this method become evident, however, when a fragmented or multistage fracture must be treated. The individual wires are not sufficient to protect a fracture in the axial direction or against rotation. To preserve the length of the bone and to protect against rotational movements, only a stiff and rigid implant is suitable, preferably one which may be locked by screws inserted proximally and distally to the fracture area.

The tibia intramedullary nails known in the prior art, which create an axial stability and a rotational stability of the fracture, have a short proximal end segment, or crown hook, and a distal segment having a straight part with a rounded tip, which simplifies stringing together of the fragments. However, as described above, these nails are rather severely deformed when inserted, so that the nail can bend plastically in the longitudinal direction. If four-fifths of the tibia nail is driven in, the crown hook penetrates the tuberositas tibia, and thereby relieves the bending demand made upon the stud. This relief can be such that when the stud is fully driven in, it lies loosely in the medullary cavity.

SUMMARY OF THE INVENTION

The invention comprises a hollow one-piece tibia intramedullary nail having a proximal end segment, a bent intermediate segment and a distal end segment. The distal end segment may be straight or it may have an intermediate portion and a terminal portion positioned at an angle to the intermediate portion. The central axis of the proximal end segment diverges from the central axis of the distal end segment or the central axis of the intermediate portion of the distal end segment at an angle in the range of about $-8°$ to about $-18°$, preferably in the range of about $-13°$ to about $-17°$ and most preferably in the range of about $-10°$ to about $-12°$. The negative values indicate a counterclockwise displacement from the axis of the distal segment or the intermediate portion thereof.

According to the invention, the proximal end segment and the intermediate segment of the nail have a total length in the range of about 80 to about 150 mm, preferably in the range of about 100 to about 110 mm. Further the sum of the length of the proximal end segment and half of the length of the intermediate segment corresponds to 25–37%, preferably to 30–35% and most preferably to 33–34% of the total length of the nail.

The proximal end segment, or crown hook, of the present invention is much longer than those known in the art. For example, the nail according to U.S. Pat. No. 4,522,202 has a proximal end segment and an intermediate bent segment which correspond only to about 19% of the total length of the nail. The proximal end segment according to the invention enters the medullary cavity much sooner, whereby it prevents excessive bending or bending pressure on the intramedullary nail.

The distal end segment of a nail according to the invention serves as a gliding surface when the nail is driven into the posterior cortex. It can be a single straight element but preferably comprises a straight terminal portion and a straight intermediate portion whose central axes intersect each other at an angle in the range of about $+120$ to about $+4°$, the positive value indicating a clockwise displacement from the axis of the intermediate portion.

DESCRIPTION OF THE DRAWINGS

The invention will be further described with reference to the drawings wherein.

DETAILED DESCRIPTION OF THE INVENTION

Figures 1, 2:
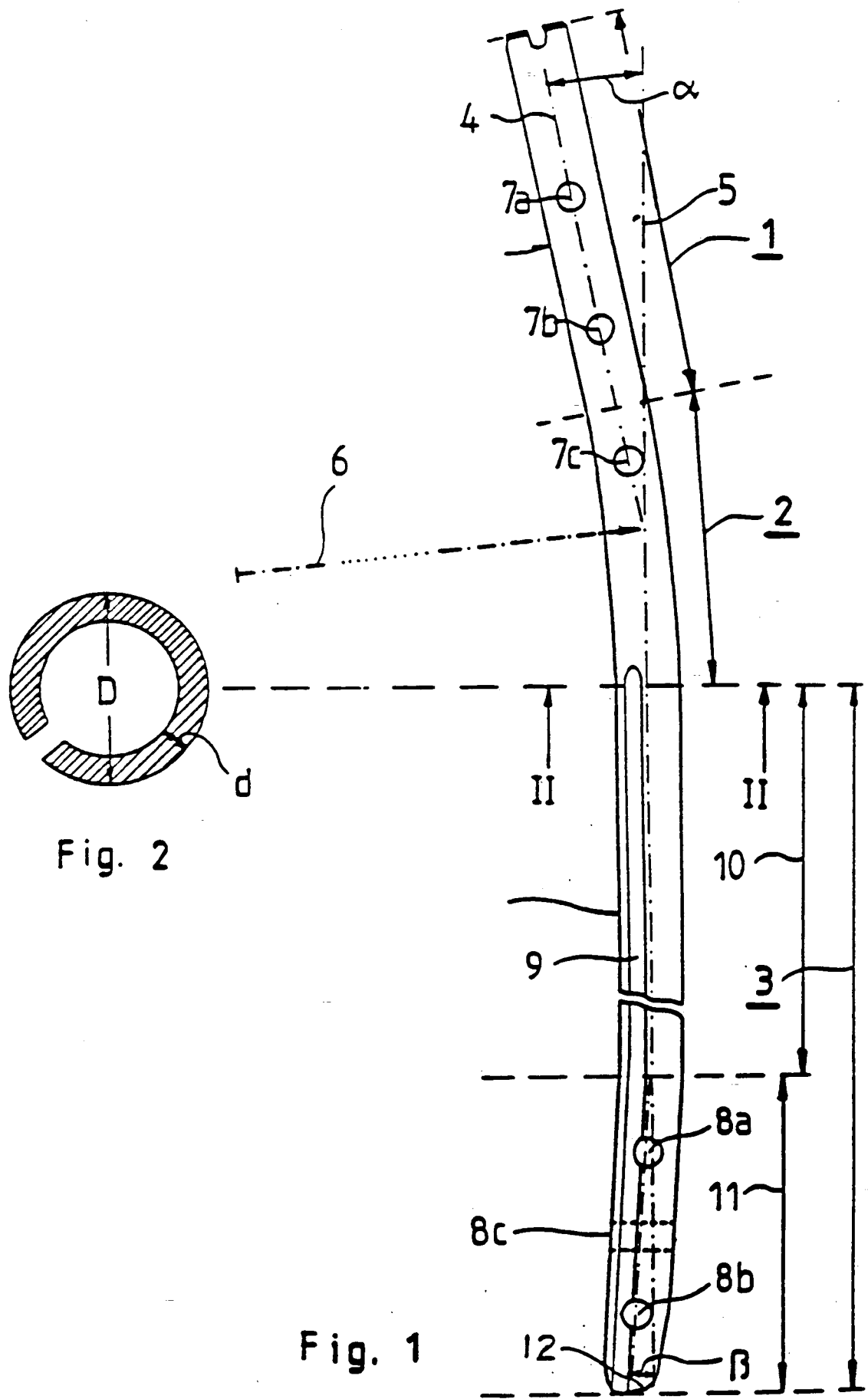
FIG. 1 is an elevational view, partly interrupted, of a nail according to the invention.
FIG. 2 is a section along line II—II of FIG. 1.

The invention provides an intramedullary nail for the treatment of lower leg fractures of all indications. Its shape is adapted to the anatomy of the medullary cavity and facilitates implantation. Two advantages of this tibia nail are that it can be inserted into the medullary cavity without plastic deformation and that it acts as a stable splint after its insertion.

The tibia nail according to the invention has a proximal end segment, a bent intermediate segment and a distal end segment. The distal end segment is preferably made in two portions, an end portion and an intermediate portion, with the end portion preferably canted toward the axis of the intermediate portion. This distal end segment provides a sliding surface when the nail is driven into contact with the posterior cortex. The angle of impact of the nail is thus more acute, and the nail has a greater tendency to follow the geometry of the medullary cavity.

The proximal end segment, also called the crown hook, is a great deal longer than those of tibia intramedullary nails known in the art. It penetrates the medullary cavity much earlier and thereby avoids an excessive bending of or bending pressure on the nail. The three-dimensional distortion of the nail when it is driven in is thereby greatly lessened If the nail is fully driven in, this exceptionally long crown hook is adjacent to the anterior cortex. The advantage of this configuration is that the tibia has the best possible splint, even without supplementary elements.

When intramedullary nails known in the art are driven in, they twist, but then lie loose in the medulla. Because of its anatomically adapted shape, a nail according to the invention can be inserted into the medullary cavity relatively simply and without excessive demands on the implant or the bone, and when it has been driven in, it forms a positive connection with the bone. This basic difference has a still greater effect when implantation must be followed by a locking operation, in which the implant must secure the length as well as the rotation of the bone. Locking intramedullary nails have thicker walls, and their resistance to bending is approximately 80% greater. To implant a prior-art locking intramedullary nail, the operator must over-ream the medullary cavity by 1.0 to 2.0 mm. This procedure has the disadvantage that a relatively large amount of vital bone is milled out, without achieving greater stability of the osteosynthesis.

An intramedullary nail according to the invention has considerable advantages over the intramedullary bunch-nailing method. As mentioned earlier, in marrow bunch-nailing the splinting of the long bone is exclusively internal. In this method, the marrow area, mostly undrilled, is filled with wires approximately 2.0 mm thick. The quality of such an osteosynthesis is largely dependent on the surgeon's skill, because it is not easy to insert these wires into the medullary cavity without getting them crossed and thereby creating bottlenecks in the cavity through which no more wires can be fed. The indications for this nailing method are very limited, since the medullary cavity is hourglass-shaped and thus has only a short narrow segment that can be sufficiently filled with wires and can thus be stabilized. When using the intramedullary bunch-nailing method, it is not possible to maintain the tibia length or to prevent rotation in the case of fragmented or multistage breaks. In caring for a multistage fracture, a fragmented fracture, or a fracture in a relatively distal or proximal location, both the length and the rotation can be secured by means of a nail according to the invention.

The nail of the invention is optimally adapted to the anatomy, since it is a relatively stiff implant which can withstand the full load that bears of the tibia. The forces operating on the tibia axially, as well as the torsional moments, are preferably carried via locking screws to the intramedullary nail. These locking screws are proximal and distal to the fracture zone, and guarantee optimum immobilization of the fracture.

In a preferred embodiment of the invention, there are three proximal holes, appropriately positioned in the frontal plane of the nail, which receive locking screws. The advantage of this configuration is that the drilling for the insertion of the screw can be done in the medial to lateral direction. The advantage of this orientation of the screws is that no blood vessels need be injured. The orientation of the proximal locking holes, at 90° to the longitudinal axis, facilitates the use of the same nails for both the right and the left tibia.

The distal locking can be done in either the frontal or the sagittal planes. In very distal fractures, sagittal locking is preferred to front locking, since tissue coverage of the screw heads may be problematic. In the use of short tibia intramedullary nails, tissue coverage in the sagittal plane is difficult. For this reason, in this type of locking, distal locking should appropriately be done in the medial to lateral direction.

Referring to the drawing, FIGS. 1 and 2 show an intramedullary nail according to the invention. The nail may be made of any customary implant material. It is hollow. In a preferred embodiment the exterior diameter D at maximum thickness is 16 mm and the wall thickness d, is 1.2 mm, though in general the wall thickness can vary from about 0.9 to about 1.3 mm, preferably from about 1.15 mm to about 1.25 mm.

The nail has a proximal end segment 1, a bent intermediate segment 2 and a distal end segment 3. The distal end segment 3 is shown made in two portions, a straight terminal portion 11 and a straight intermediate portion 10. The central axis of the terminal portion intersects the central axis of the intermediate portion at an angle $\beta$ of about +2°. This angle $\beta$ may range up to about +4°.

The distal end segment may, if desired, be made in a single integral piece, i.e. $\beta$ may be 0°.

According to the convention used here a positive value of angular displacement indicates a clockwise displacement from the reference point, in this case the central axis of the intermediate portion 10 of the distal end segment 3.

The proximal end segment has a central axis which is inclined to the axis of the distal end segment at an angle $\alpha$, of from about −8° to about −18° preferably from about −13° to about −17°, but most preferably between about −10° and about −12°. Reference to the axis of the distal end segment means reference to axis of the intermediate portion of the distal end segment.

The bent section 2 of the nail has a radius of curvature 6 which may range from about 100 to about 120 mm, preferably from about 105 to about 115 mm.

The proximal end segment 1 and the bent intermediate segment 2 have a total length of from about 80 to about 150 mm, preferably between about 100 to 110 mm, usually about 105 mm. The sum of the length of the proximal end segment and one half the length of the intermediate segment is usually about $\frac{1}{3}$ the total nail length but may be from about 25% to about 37%, preferably from about 30 to about 35%, most preferably from about 33 to about 34%, of the total length of the nail.

A nail according to the invention may be provided with holes for transverse locking screws or bolts. In the embodiment shown in FIG. 1, there are three medio-lateral locking holes 7a, 7b and 7c in the proximal segment 1 and three holes 8a, 8b and 8c in the distal end segment 3. Holes 8a and 8b are in the frontal plane (medio-lateral) and hole 8c is in the sagittal plane (antero-posterior). Holes 8a and 8b are positioned proximally and distally from the center of terminal portion 11 and hole 8c is located at the center of the terminal portion 11.

The number of holes for locking screws may be varied depending on the proposed use and length of the nail.

The nail shown in FIG. 1 also has a slot shaped recess 9 generally parallel to the central axis of the distal end segment 3. Recess 9 extends from the bent intermediate segment 2 to the tip of the distal end segment 3.

The posterior side of the terminal portion 11 of the distal end segment may be bevelled as at 12.

We claim:

1. A hollow one-piece intramedullary nail for the tibia comprising a proximal end segment having a central axis, a bent intermediate segment and a distal end segment having a central axis, wherein:
   (a) the central axis of the proximal end segment diverges from the central axis of the distal end segment at an angle in the range of from about $-8°$ to about $-18°$;
   (b) the proximal end segment and the intermediate segment have a total length in the range of about 80 to about 150 mm; and
   (c) the sum of the length of the proximal end segment and half of the length of the intermediate segment is from about 25 to about 37% of the total length of the nail.

2. A nail according to claim 1, wherein the sum of the length of the proximal end segment and half of the length of the intermediate segment is from about 30 to about 35% of the total length of the nail.

3. A nail according to claim 2, wherein the sum of the length of the proximal end segment and half the length of the intermediate segment is from about 33% to about 34% of the total length of the nail.

4. A nail according to claim 1, wherein the distal end segment comprises a straight terminal portion and a straight intermediate portion each having a central axis, the axis of the terminal portion intersecting the axis of the intermediate portion at an angle in the range of from about $+1°$ to about $+4°$.

5. A nail according to claim 1, wherein the angle between the proximal end segment and the distal end segment is from about $-13°$ to about $-17°$.

6. A nail according to claim 1, wherein the angle between the proximal end segment and the distal end segment is from about $-10°$ to about $-12°$.

7. A nail according to claim 1, wherein the proximal end segment and the intermediate segment have a total length in the range of about 100 to about 110 mm.

8. A nail according to claim 4, wherein the straight terminal portion of the distal end segment has at least one medio-lateral locking hole and at least one antero-posterior locking hole.

9. A nail according to claim 8, wherein the straight terminal portion of the distal end segment has two medio-lateral locking holes one located proximally and the other distally from the center of said straight terminal portion, and one antero-posterior locking hole located at the center of said straight terminal portion.

10. A nail according to claim 4, wherein said straight terminal portion has a posterior bevelling.

11. A nail according to claim 4, wherein said bent intermediate segment has a radius of curvature between about 100 and about 120 mm.

12. A nail according to claim 4, wherein said bent intermediate segment has a radius of curvature between about 105 and about 115 mm.

* * * * *

UNITED STATES PATENT AND TRADEMARK OFFICE
CERTIFICATE OF CORRECTION

PATENT NO. : 5,041,115
DATED : August 20, 1991
INVENTOR(S) : Robert Frigg

It is certified that error appears in the above-identified patent and that said Letters Patent is hereby corrected as shown below:

Col. 2, line 45, delete "+120" and insert --+1°--.

Signed and Sealed this

Sixth Day of October, 1992

Attest:

DOUGLAS B. COMER

*Attesting Officer*      *Acting Commissioner of Patents and Trademarks*